United States Patent
Rangasamy et al.

(10) Patent No.: US 11,903,961 B2
(45) Date of Patent: Feb. 20, 2024

(54) HEMOSTATIC AGENT AND METHOD OF PRODUCTION THEREOF

(71) Applicant: AMRITA VISHWA VIDYAPEETHAM, Kochi (IN)

(72) Inventors: Jayakumar Rangasamy, Kochi (IN); Nivedhitha Muthiahpillai Sundaram, Kochi (IN); Ullas Mony, Kochi (IN); Praveen Kerala Varma, Kochi (IN)

(73) Assignee: Amrita Vishwa Vidyapeetham, Kochi (IN)

( * ) Notice: Subject to any disclaimer, the term of this patent is extended or adjusted under 35 U.S.C. 154(b) by 130 days.

(21) Appl. No.: 17/404,688

(22) Filed: Aug. 17, 2021

(65) Prior Publication Data
US 2022/0054529 A1 Feb. 24, 2022

(30) Foreign Application Priority Data

Aug. 18, 2020 (IN) .............................. 202041035602

(51) Int. Cl.
*A61K 31/722* (2006.01)
*A61K 33/06* (2006.01)
(Continued)

(52) U.S. Cl.
CPC ............ *A61K 31/722* (2013.01); *A61K 33/06* (2013.01); *A61L 26/008* (2013.01);
(Continued)

(58) Field of Classification Search
None
See application file for complete search history.

(56) References Cited

U.S. PATENT DOCUMENTS 8,450,553 B2   5/2013   Utterberg et al.
9,168,325 B2   10/2015  Goessl et al.
(Continued)

FOREIGN PATENT DOCUMENTS

CN        103937023 B      5/2016
WO    WO-2010031995 A2 *  3/2010    ............. A61F 13/36

OTHER PUBLICATIONS

Komentaku et al., "Chitosan dressings containing inorganic additives and levofloxacin as potential wound care products with enhanced hemostatic properties" International Journal of Biological Macromolecules vol. 162 pp. 693-703 https://doi.org/10.1016/j.ijbiomac.2020.06.187 (Year: 2020).*

(Continued)

*Primary Examiner* — Eric Olson
(74) *Attorney, Agent, or Firm* — Foley & Lardner LLP

(57) ABSTRACT

A composition and method of preparing the composition for rapid and effective hemostasis is provided. The composition includes a first agent to induce platelet plug formation, a second to induce vasoconstriction and a third agent for activation of coagulation cascade. The composition comprises of 0.01% to 5% of chitosan; 0.01% to 0.25% of potassium aluminum sulphate; and 0.01% to 0.25% calcium salt. The clotting time of the composition is in the range of 30s to 140s. A method of preparing the hemostatic composition is further disclosed. The composition is configured to control hemorrhage from oozing and pressured bleeding injury any site in human/animal body.

12 Claims, 14 Drawing Sheets

(51) Int. Cl.
*A61P 7/04* (2006.01)
*A61L 26/00* (2006.01)
*C08J 3/075* (2006.01)

(52) U.S. Cl.
CPC ....... *A61L 26/0023* (2013.01); *A61L 26/0095* (2013.01); *A61P 7/04* (2018.01); *C08J 3/075* (2013.01); *A61L 2400/04* (2013.01); *C08J 2305/08* (2013.01)

(56) References Cited

U.S. PATENT DOCUMENTS

| | | | |
|---|---|---|---|
| 2007/0237811 A1* | 10/2007 | Scherr | A61L 26/0085 424/445 |
| 2011/0046262 A1* | 2/2011 | Bublewitz | A61K 6/18 523/121 |
| 2017/0049696 A1 | 2/2017 | Chevrier et al. | |
| 2018/0078672 A1 | 3/2018 | Koryagin et al. | |
| 2018/0110897 A1* | 4/2018 | Bush | A61K 47/14 |

OTHER PUBLICATIONS

Tarighi et al., "A review on common chemical hemostatic agents in restorative dentistry" Dental Research Journal vol. 11 No. 4 pp. 423-428 (Year: 2014).*
InChem data sheet for calcium chloride, downloaded from https://inchem.org/documents/icsc/icsc/eics1184.htm (Year: 2012).*
Nivedhitha et al., "Injectable Nano Whitlockite Incorporated Chitosan Hydrogel for Effective Hemostasis" ACS Applied Biomaterials vol. 2 pp. 865-873 DOI: 10.1021/acsabm.8b00710 (Year: 2019).*

* cited by examiner

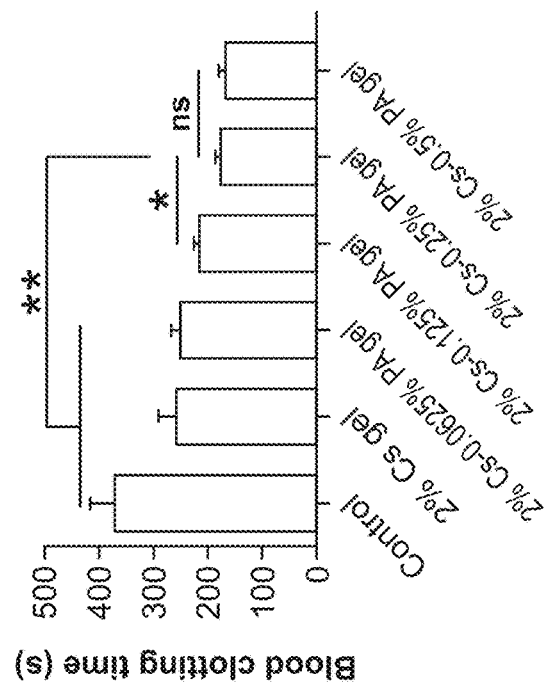
FIG. 7A
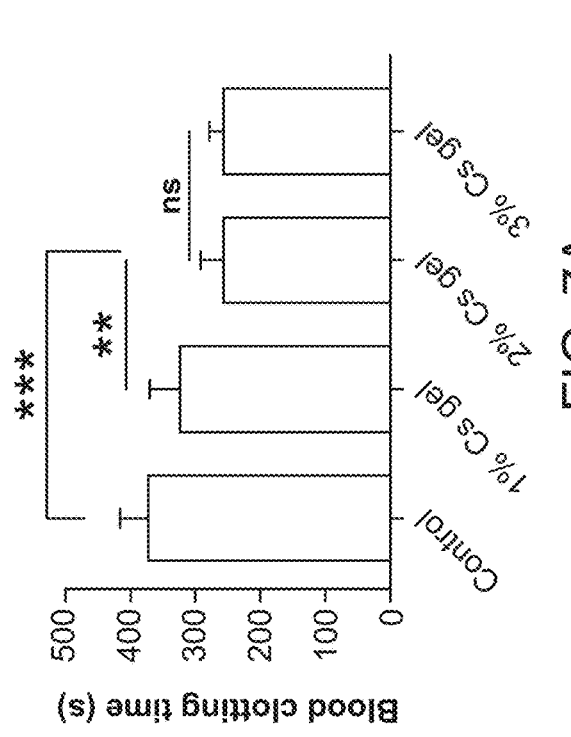
FIG. 7C
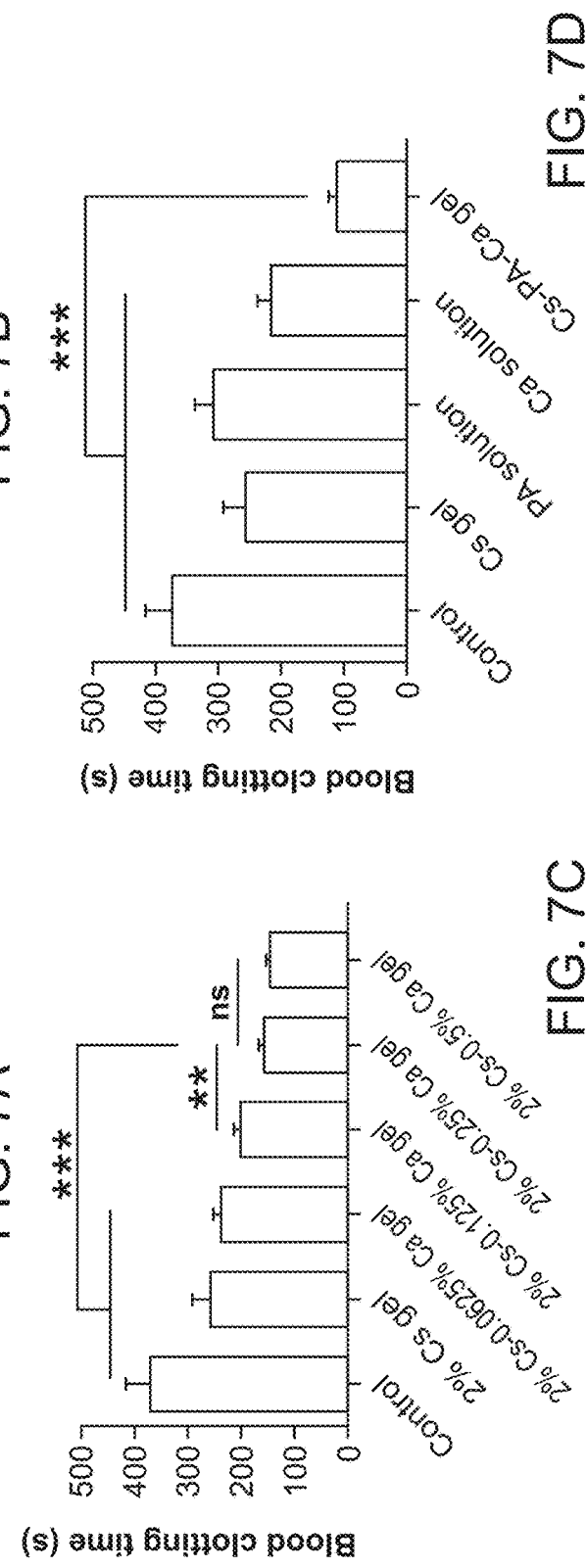
FIG. 7B
FIG. 7D

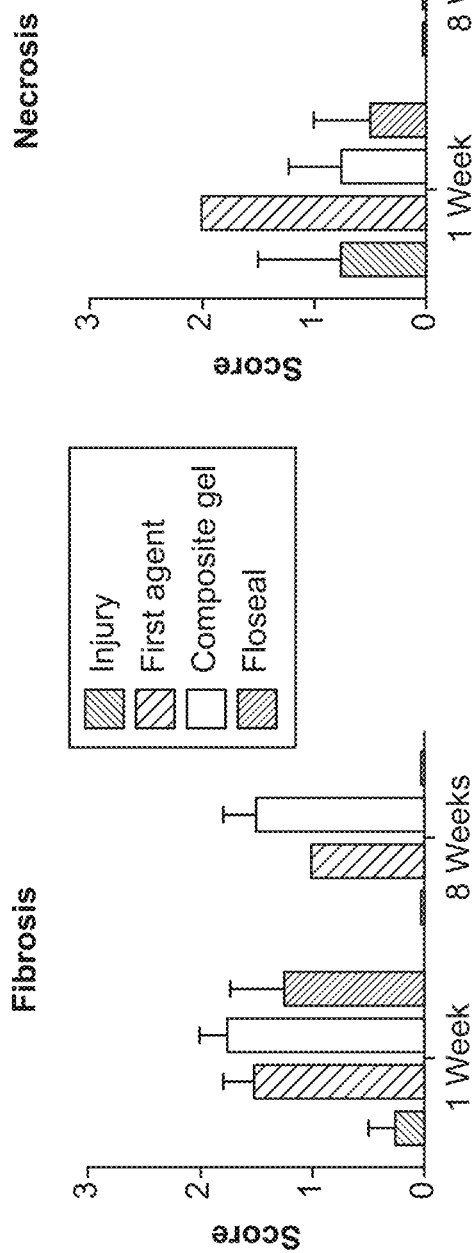
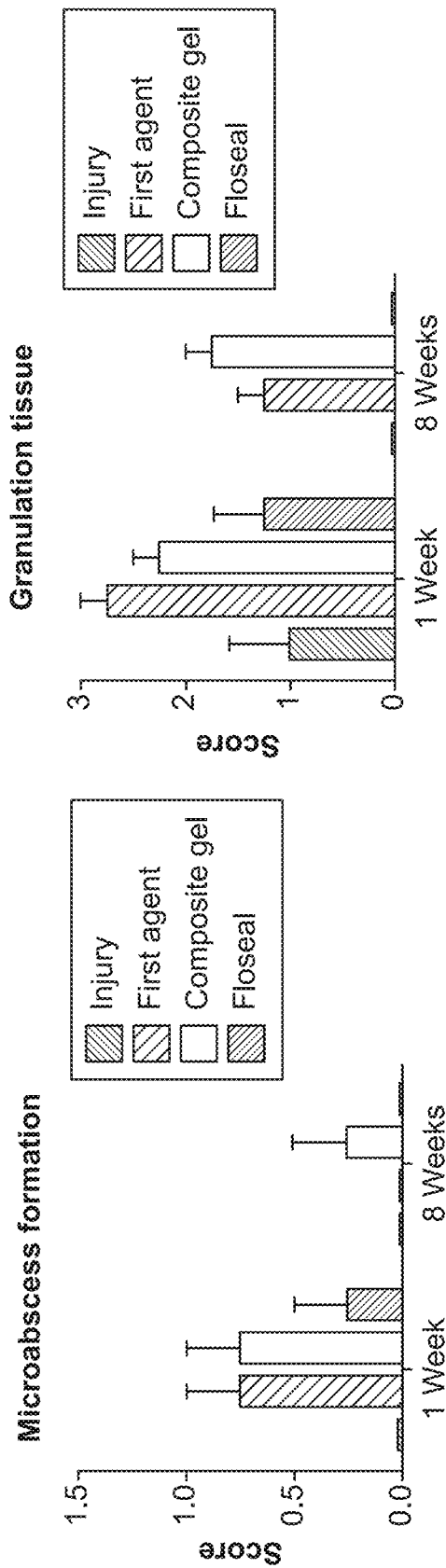
FIG. 12A
FIG. 12B
FIG. 12C
FIG. 12D

HEMOSTATIC AGENT AND METHOD OF PRODUCTION THEREOF

CROSS-REFERENCES TO RELATED APPLICATIONS

This application claims priority to Indian patent application No. 202041035602 entitled HEMOSTATIC AGENT AND METHOD OF PRODUCTION THEREOF filed on Aug. 18, 2020.

FIELD OF THE INVENTION

The present invention is generally related to agents for bleeding control, and in particular to a composition and method for rapid and effective hemostasis.

BACKGROUND AND DESCRIPTION OF RELATED ART

Hemostasis is a process of restricting blood loss when there is damage to blood vessel or an organ. There are three main mechanisms involved in hemostasis: vasoconstriction, platelet plug formation and activation of coagulation cascade. Vasoconstriction refers to the step when there is damage to blood vessel the smooth muscles contracts and tries to minimize blood that is lost. Platelet plug formation refers to the steps of activation of platelets due to the damage caused in blood vessel and blood cells get exposed to collagen fibers. These activated platelets come together and forms a plug there by sealing the injured site. Activation of coagulation cascade refers to coagulation cascade activated by both intrinsic and extrinsic pathways. The two pathways come together in the final common pathway. Calcium or magnesium or other divalent ions and their combinations play an important role in the activation of coagulation cascade.

Uncontrolled blood loss is a serious problem when there is massive trauma or during surgical procedures. Hemostatic agents or procedures help in controlling bleeding when the normal hemostasis mechanism is not effective. These are different mechanical, thermal and chemical agents used to achieve hemostasis. This includes use of cauterization, manual pressure using gauze and sutures, but these procedures are time consuming and might not help in achieving effective hemostasis.

US patent publication US20180078672A1 describes a hemostatic agent having an active gelling agent with a three-dimensional cross linked structure. The hemostatic agent comprise of chitosan or its derivatives, organic calcium compound, organic acid and water. US patent publication US20170049696A1 describes a freeze-dried polymer composition comprising chitosan and at least one lyoprotectant for reconstitution in platelet-rich plasma, blood products and their combinations. Chinese patent CN103937023B describes a preparation method of light body calcium alginate base cavernous body functional material comprising sodium alginate powder, soluble calcium salt, magnesium salts or aluminum salt, reinforcing agent, peroxide, and catalyst mix.

U.S. Pat. No. 9,168,325B2 describes a pharmaceutical hemostatic liquid foam base preparation comprising albumin as foaming agent, a fibrinogen precipitating substance and optionally a coagulation inducing agent. The albumin as foaming agent is present in native form. U.S. Pat. No. 8,450,553B2 describes a pad of elastomeric material for achieving hemostasis on any bleeding site. The pad exhibits hemostatic and leak prevention properties against needle puncture holes in the skin or the wall of a hollow medical device.

Although several agents and methods are known in the art, the drawbacks of these agents are that when in a sponge or powder form they would not completely cover the bleeding site to bring about effective hemostasis. Liquid hemostatic agents like fibrin glue require extremely dry environment to form a firm seal and control bleeding. They also require sensitive handling procedures. Biologically active agents such as fibrin or thrombin incorporated hemostatic agents have a risk of disease transmission and has also reported to show immunological responses. There is therefore need for effective solution to the abovementioned problems.

SUMMARY OF THE INVENTION

The present invention in its various embodiments provides a hemostatic composition, dosage forms thereof, a method of producing such compositions, and a method of administering such compositions for effecting hemostasis. In various embodiments, included herein is a hemostatic hydrogel composition and its method of preparation for rapid and synergistic bleeding control.

In various embodiments, a hemostatic hydrogel composition for rapid and synergistic bleeding control is disclosed. In one embodiment, the composition comprises of 0.01% to 5% of chitosan; 0.01% to 0.25% of potassium aluminum sulphate; and 0.01% to 0.25% calcium salt. The clotting time of the composition is in the range of 30s to 140s.

In another embodiment of said composition, hydrogel may be shaped into a morphology selected from sponge, flexible bandage, scaffold, injectable gel, foam, cream and powder form.

In yet another embodiment of said composition, the composition is stable at a temperature range of 25 to 50° C.

In yet another embodiment of said composition, composition shows one more more characteristics selected from a hemolytic potential of less than 5 percent, a RBC aggregation of at least 0.2, a platelet aggregation of at least 0.4, and adhesion strength of 6-10 kPa.

In yet another embodiment of said composition, the chitosan has molecular weight in the range of 25 kDa to 1000 kDa. The chitosan exhibits an average degree of deacetylation in the range of 40% to 99% and degree of acetylation in the range of 1% to 70%.

In various embodiments, a method of preparing a hemostatic composition is disclosed. In the first step 0.01% to 5% of chitosan powder is added in acetic acid under continuous stirring to form a chitosan solution. To adjust the pH of the chitosan solution sodium hydroxide is then added drop wise under continuous stirring. The solution is then subjected to centrifugation to form chitosan hydrogel. The chitosan hydrogel is then mixed with 0.01% to 0.5% of potassium aluminum sulphate under vigorous stirring to form a homogeneous mixture. Finally 0.01% to 0.5% calcium chloride is added to the homogeneous mixture under vigorous stirring to obtain the homogenous mixture of composite hydrogel.

In one embodiment of the method, the pH of the chitosan solution is in the range of 6-7.

This and other aspects are described herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 7A illustrates bar graph representing the in vitro blood clotting study with optimization percentage of First agent (Cs hydrogel) in recalcified whole blood FIG. 7B illustrates bar graph representing the in vitro blood clotting study with optimization percentage of Second agent (PA) in recalcified whole blood FIG. 7C illustrates bar graph representing the in vitro blood clotting study with optimization percentage of Third agent (Ca) of Cs-Pa-Ca composite hydrogel in recalcified whole blood FIG. 7D illustrates bar graph representing the in vitro blood clotting study with optimization percentage of individual components of composite hydrogel in recalcified whole blood

FIG. 12A illustrates bar graphs representing histophathological evaluation: in the fibrosis of the developed hemostatic composition at the site of application.

FIG. 12B illustrates bar graphs representing histophathological evaluation in necrosis of the developed hemostatic composition at the site of application.

FIG. 12C illustrates bar graphs representing histophathological evaluation in microabscess formation of the developed hemostatic composition at the site of application.

FIG. 12D illustrates bar graphs representing histophathological evaluation in granulation tissue formation of the developed hemostatic composition at the site of application.

DETAILED DESCRIPTION OF THE EMBODIMENTS

Figure 1:
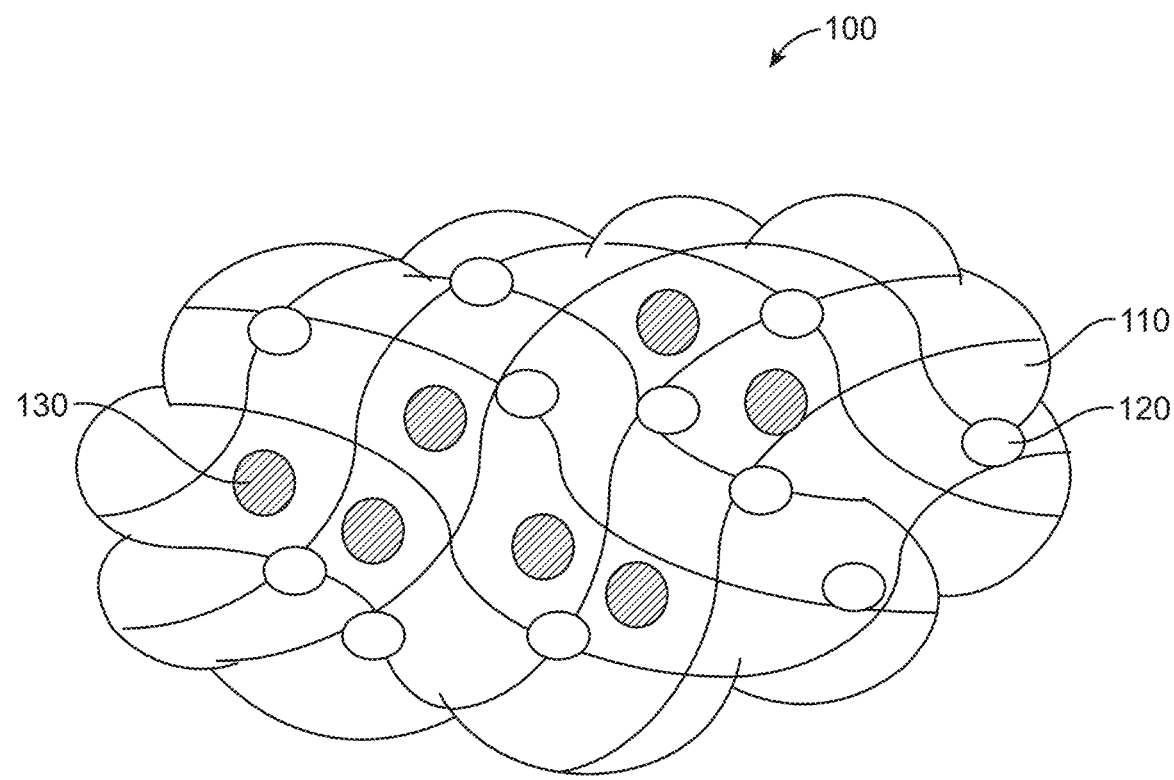
FIG. 1 shows a schematic diagram of a hemostatic composition.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The present invention in its various embodiments is directed to hemostatic compositions, dosage forms thereof, a method of producing such compositions, and a method of administering such compositions for effecting hemostasis.

In various embodiments, provided herein is a hemostatic composition (100) comprising an therapeutically effective amount of at least a first agent (110) to induce platelet plug formation, a second agent (120) to induce vasoconstriction, and a third agent (130) to activate coagulation cascade. In one embodiment, the composition includes as first agent 110 at least one or more polycationic polymer or polysaccharide that is capable of aggregating blood cells and forming a strong plug to stop bleeding. In one embodiment, the composition includes one or more astringent 120 that would cause vasoconstriction by aggregating blood proteins and coagulation factors that help in controlling blood loss. In one embodiment, the composition includes of one or more coagulation activator 130 that could accelerate the coagulation cascade to achieve rapid bleeding control.

In some embodiments, the first agent (110) includes a base material that is a synthetically or naturally derived material selected from a group consisting of a cationic polymer, a polysaccharide, a protein, an electrostatic agent, and an amine group containing polymer. In some embodiments, the base material is configured to electrostatically interact and aggregate blood cells when in contact. In one embodiment, the base material may be a cationic polymer or a polysaccharide and may include amine groups. In one embodiment, the base material includes a polymer or a polysaccharide including α-chitin, β-chitin, γ-chitin, α-chitosan, β-chitosan, N-acetyl glucosamine, a combination thereof, or a derivative thereof.

In some embodiments, the second agent 120 includes one or more of an astringent or a vasoconstrictor to induce vasoconstriction in a subject. In one embodiment, the astringent is selected from the group selected from aluminum salts including alum, potassium aluminum sulfate, aluminum ammonium sulfate, aluminum sulfate, or aluminum chloride hydrate, aluminum based ceramics/composites and other agents including ferric sulfate, ferric chloride, zinc chloride, tannins, and mixtures thereof. In one embodiment, the vasoconstrictor is selected from the group selected from a vasoactive catecholamine, a vasoactive peptide, and mixtures thereof. In one embodiment, the astringent includes alum or potassium aluminum sulfate.

In some embodiments, the third agent 130 includes one or more coagulation cascade activator selected from calcium, magnesium and other divalent containing compounds and their combinations that could be selected from a group consisting of calcium chloride ($CaCl_2$), calcium oxide (CaO), calcium hydroxide ($Ca(OH)_2$), calcium nitrate ($Ca(NO_3)_2$), calcium carbonate ($CaCO_3$), calcium oxalate ($C_2H_2CaO_5$), magnesium chloride ($MgCl_2$), magnesium oxide (MgO), magnesium hydroxide ($Mg(OH)_2$), magnesium nitrate ($Mg(NO_3)_2$), magnesium carbonate ($MgCO_3$), pigeonite, ceramics, minerals containing calcium, magnesium, iron, silica, zinc, or bismuth, microparticles thereof, nanoparticles thereof, and powder thereof. In some embodiments, the third agent includes a coagulation cascade activator of biological (human or animal) or synthetic origin, or mixtures thereof. In one embodiment, the third agent includes calcium chloride.

In some embodiments, the composition includes chitosan, alum or potassium aluminum sulfate, and calcium or magnesium salts as the first, second and third agents, respectively. The three agents act simultaneously by forming platelet plug, causing vasoconstriction by precipitating plasma proteins and also activating coagulation cascade. In some embodiments, the composition simultaneously causes one or more events in a subject, selected from RBC aggregation, platelet and plasma protein aggregation, and activation of coagulation cascade.

In some embodiments, the first agent, second agent and/or third agent in the composition is present at a concentration range of 0.1% to 10%.

In some embodiments, the composition includes at least one excipient formulated with the composition. The excipient may be any known excipient in the art such as a binder, vehicle, coating, sorbent, preservative, or the like. In one embodiment, the composition is an injectable hydrogel and can also be processed into sponge, flexible bandage, scaffold, gel, foam, cream or powder form. FIG. 1 illustrates a gel according to the embodiments described herein.

In one embodiment, the composition is formulated in a unit dosage form such as topical or parenteral formulation such as an injectable gel which can be further processed into various forms including but not limited to sponge, powder, foams and cream.

In one embodiment, the composition is in the form of an injectable composition such as a hydrogel, sponge, film, cream, powder, or spray foam.

In one embodiment, the composition is configured to adhere to the bleeding site. In one embodiment, the composition includes one or more adhesive agents. In one embodiment, the adhesive agent is conjugated with the one or more agents.

In various embodiments, a method 200 of preparing the composition is provided. In one embodiment, the composition is prepared by physical mixing of the three agents.

In one embodiment, the first agent in the composition is prepared by dissolving (202) α-chitosan or β-chitosan powder (1% to 5%) in glacial acetic acid or hydrochloric acid, phenyl lactic acid, poly glutamic acid under continuous stirring. To adjust the pH of the chitosan solution to be in the range 6-7 sodium hydroxide is then added 204 drop wise under continuous stirring. The solution is then subjected to centrifugation 206 to form chitosan hydrogel. The chitosan hydrogel is then mixed 208 with 0.01% to 0.5% of potassium aluminum sulphate under vigorous stirring to form a homogeneous mixture. Finally 0.01% to 0.5% calcium chloride is added 210 to the homogeneous mixture under vigorous stirring to obtain the homogenous mixture of composite hydrogel.

In one embodiment, the chitosan has an average degree of deacetylation between 40% to about 99% and degree of acetylation between 1% to about 70%. In one embodiment, molecular weight of chitosan is between 25 kDa to 1000 kDa.

In some embodiments, effective range of first agent is up to 5%, second agent up to 0.25% and/or third agent up to 0.25%. Concentration of first agent above 5% would not be injectable, concentration of second agent and third agent more than 0.25% is found to be not cytocompatible to HUVEC.

In various embodiments, provided herein is a method of using the composition for stopping bleeding during oozing and pressured bleeding conditions. In one embodiment, the composition effectively controls oozing and pressured bleeding from any site of human or animal body without a compression. In some embodiments, the composition is used for blood loss control in various applications selected from traumatic wound, dental surgery, keyhole surgery, and combat wound. In one embodiment, the composition is used for surgery, trauma, burn, wound, or injury treatment. In one embodiment, the composition is configured to prevent infection, accelerate wound healing, or stopping hemorrhage.

In some embodiments, the composition has a clotting time of less than 30 s in an oozing bleeding condition. In some embodiments, the composition has a clotting time of less than 140 s in a pressured bleeding condition.

Figure 3A:
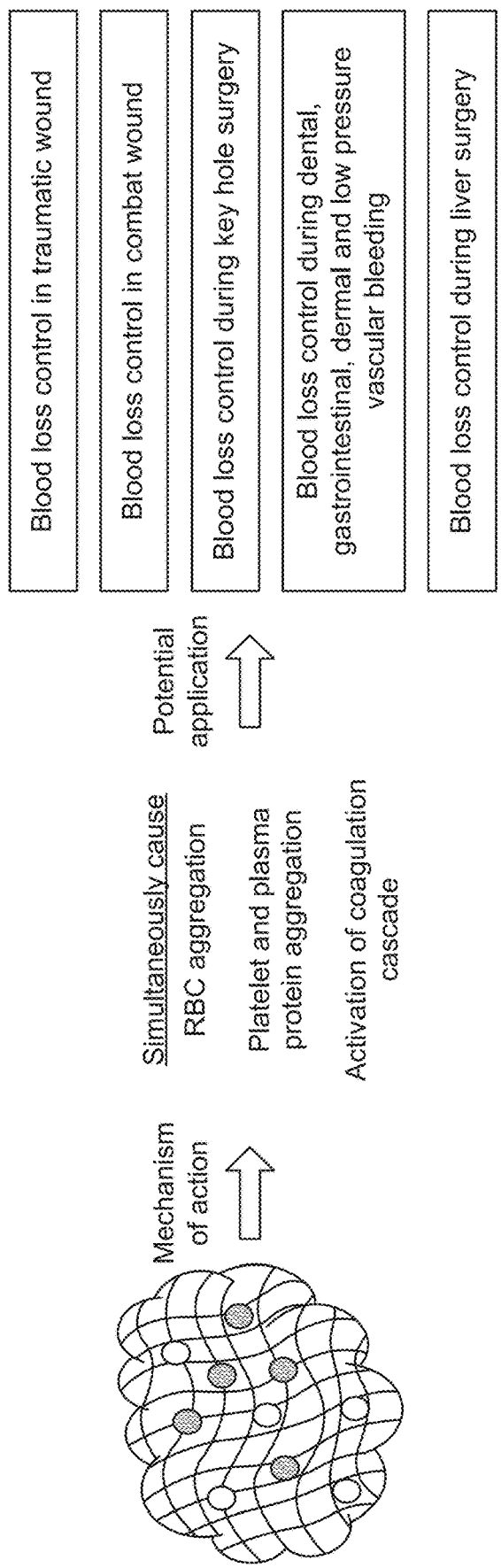
FIG. 3A shows mechanism of action and potential applications of the hemostatic composition and FIG. 3B illustrates the pictorial representation of the different forms of the hemostatic composition.

Without being bound to any particular theory, it is suggested herein that the composition acts simultaneously through the three mechanisms involved in hemostasis, i.e. vasoconstriction, platelet plug formation and activation of coagulation cascade, and brings about rapid bleeding control, as illustrated in FIG. 3A. A mechanistic action of the developed hemostatic agent and its potential application is suggested further. The composition provides better hemorrhage control as it is capable of sealing the bleeding site by aggregating blood cells and at the same time concentrating clotting factors and also activating the coagulation cascade thereby forming a strong seal at the bleeding site. The individual components of the developed hemostatic agent are relatively inexpensive. The composition is formulated in a form such as gel with the advantage of evenly confining to irregularly shape injured site and helps in achieving complete hemostasis in all types of bleeding including oozing and pressured bleeding from any site of human/animal body. They easily adapt to irregular injury site and cause effective hemostasis.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope. Further, the examples to follow are not to be construed as limiting the scope of the invention which will be as delineated in the claims appended hereto.

EXAMPLES

Example 1: Preparation of Hemostatic Agent

Figure 2:
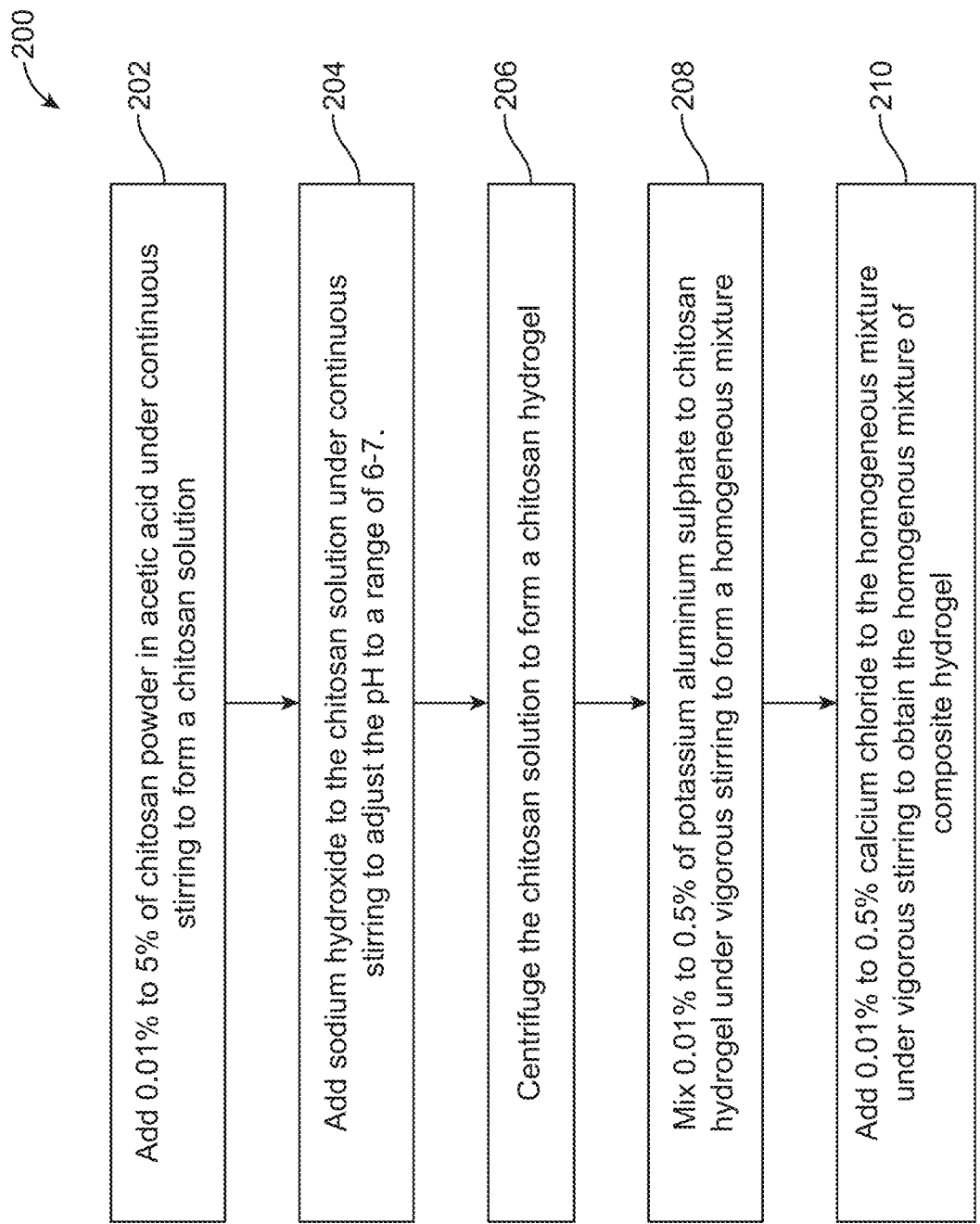
FIG. 2 shows the schematic representation of steps involved in preparation of composite hydrogel.
Figure 3B:
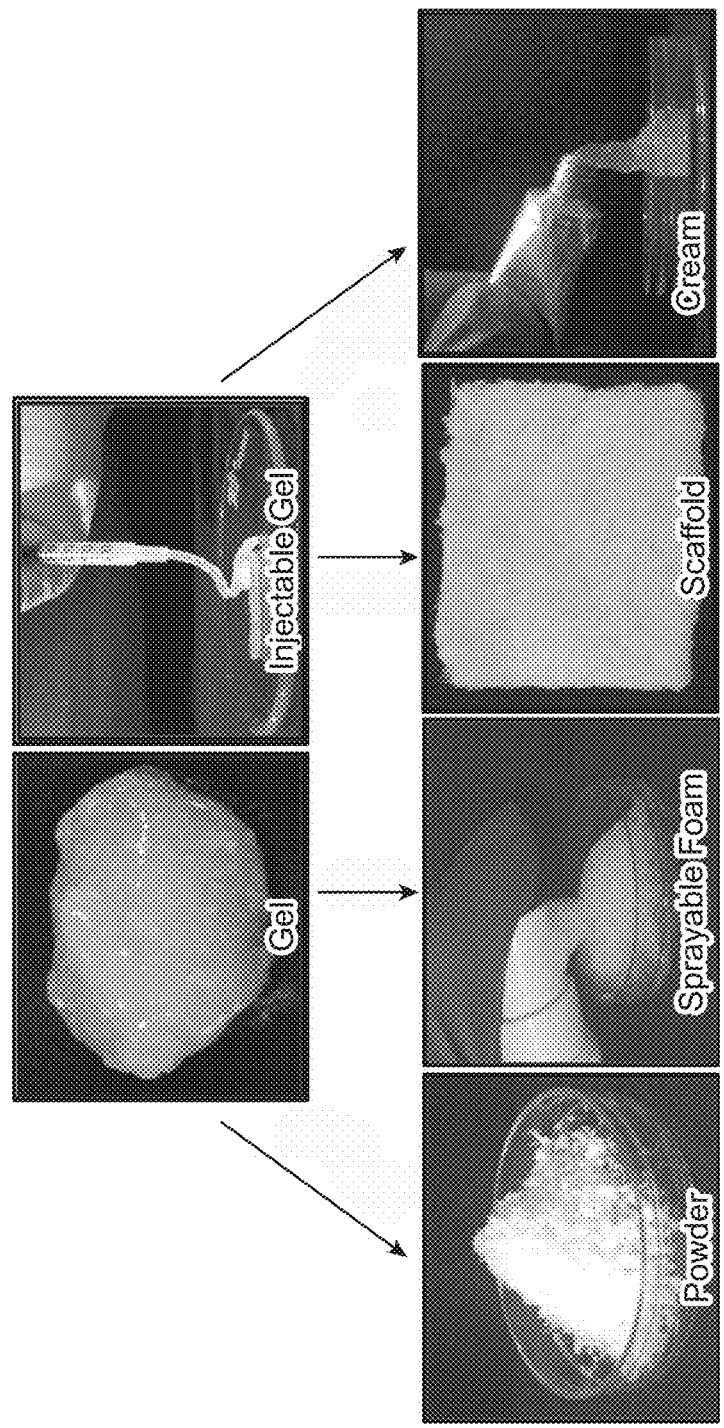

In an embodiment the first agent was prepared using chitosan (110) with average degree of deacetylation of 85% and molecular weight between 100-150 kDa. Different concentrations (1% or 2% or 3%) of chitosan hydrogel (Cs) was prepared by dissolving chitosan powder (1 or 2 or 3 g) in 1% acetic acid (100 mL) under continuous stirring at 27° C. until it is completely dissolved. Sodium hydroxide (1N NaOH) was added drop wise under continuous stirring condition to bring the pH of chitosan solution to 6.5. Chitosan hydrogel was then obtained by centrifugation at 9500 rpm for 15 mins. The obtained chitosan hydrogel was washed by centrifugation at 9500 rpm for 10 mins using double distilled water to remove excess NaOH. Second agent used was potassium aluminum sulphate (PA) (120) in the range 0.0625% to 0.5% and was added to prepared chitosan hydrogel under vigorous stirring for 5 mins to form a homogeneous mixture. Once a homogenous mixture of Cs-PA hydrogel (100) was formed different concentration of third agent-calcium chloride (Ca) (130) from 0.0625% to 0.5% was added under vigorous stirring to obtain homogenous mixture of composite (Cs-PA-Ca) hydrogel (FIG. 2). Hemostatic agent in the form of an injectable hydrogel that was prepared can be further processed into sponge, powder, foams and cream (FIG. 3B).

Example 2: Physiochemical Characterization of Developed Hemostatic Agent

Figure 4A:
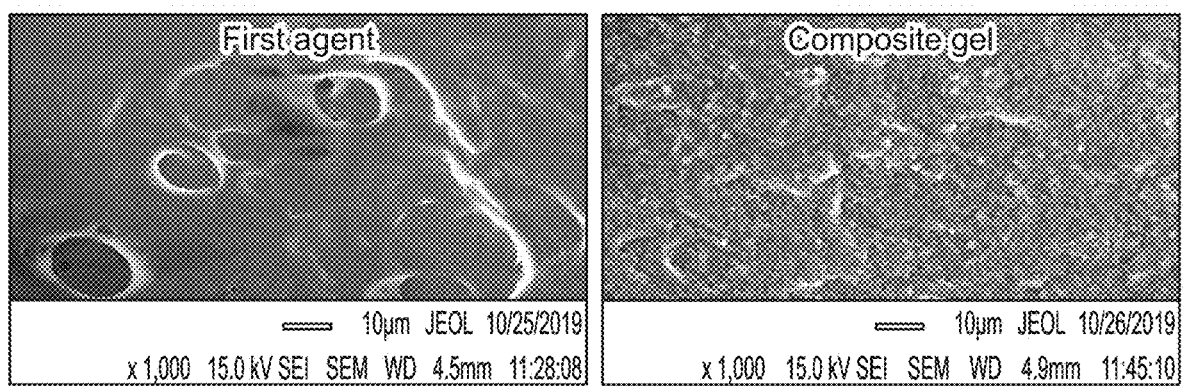
FIG. 4A shows the physiochemical characterization by FESEM images of first agent and composite gel.
Figure 4B:
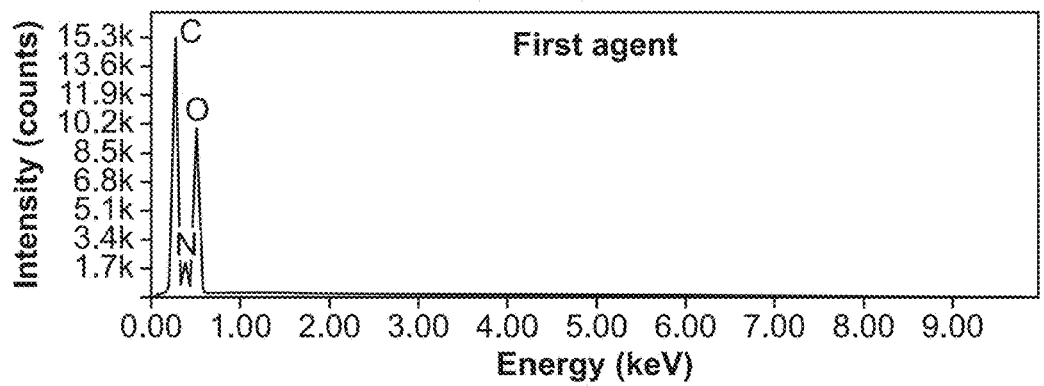
FIG. 4B shows the physiochemical characterization by EDAX of first agent and composite gel.
Figure 4B:
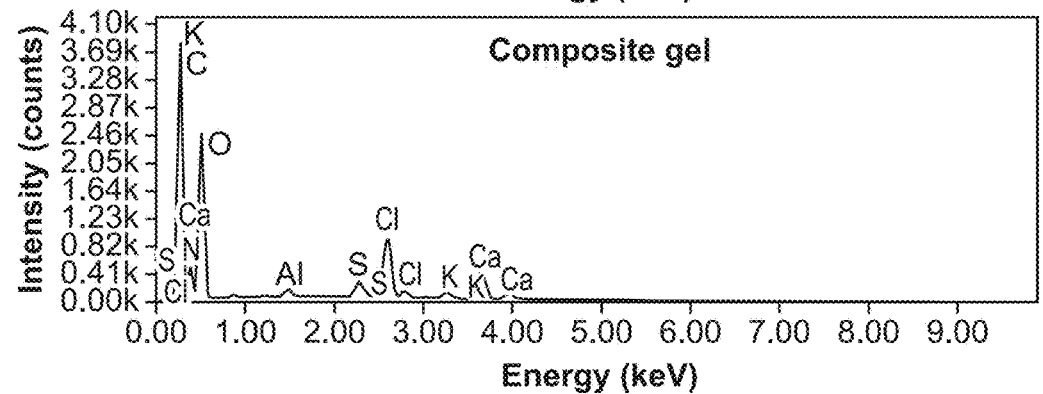
Figure 4C:
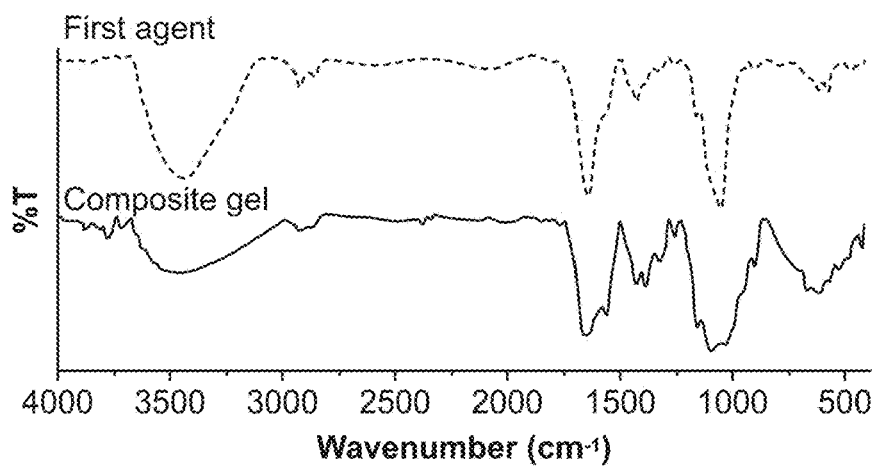
FIG. 4C shows the physiochemical characterization by FTIR spectra of first agent and composite gel.

First agent (Chitosan (Cs)) (110) and composite (Cs-PA-Ca) hydrogel was characterized by FESEM, EDAX and FTIR analysis. FESEM images (FIG. 4A) showed smooth morphology of first agent and rough morphology of composite gel due to uniform distribution of second (PA) (120) and third (Ca) (130) agent in first agent (Cs hydrogel) (110). EDAX spectra (FIG. 4B) of composite (Cs-PA-Ca) hydrogel showed peaks of C, N, O, Al, K, S, Ca and Cl which confirms the presence of first, second and third agent in composite gel. Further, FTIR spectra (FIG. 4C) of composite (Cs-PA-Ca) hydrogel had characteristic peaks of first agent (110) (2924 cm-1 (—C—H stretch)), second agent (120) (1087 cm-1 (—Al—OH vibration)) and third agent (130) (1635 cm-1(—OH vibration)) confirming its presence.

Figure 5A:
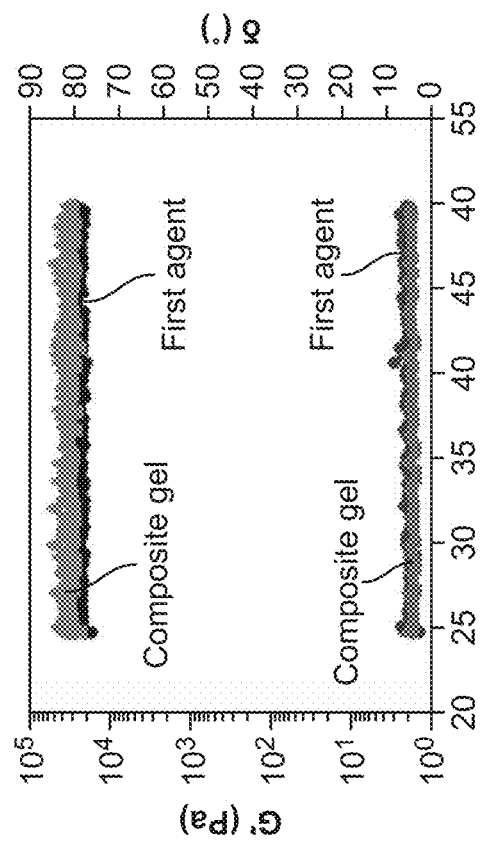
FIG. 5A illustrates graph representing rheological analysis by frequency sweep analysis of first agent and composite gel.
Figure 5B:
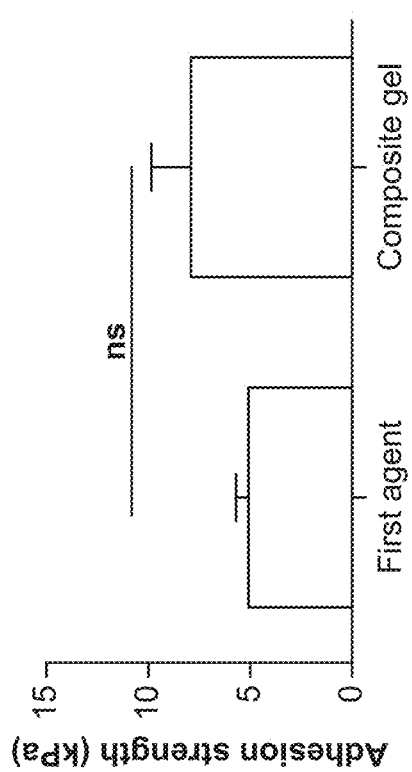
FIG. 5B illustrates graph representing rheological analysis by temperature stability study of first agent and composite gel.
Figure 5C:
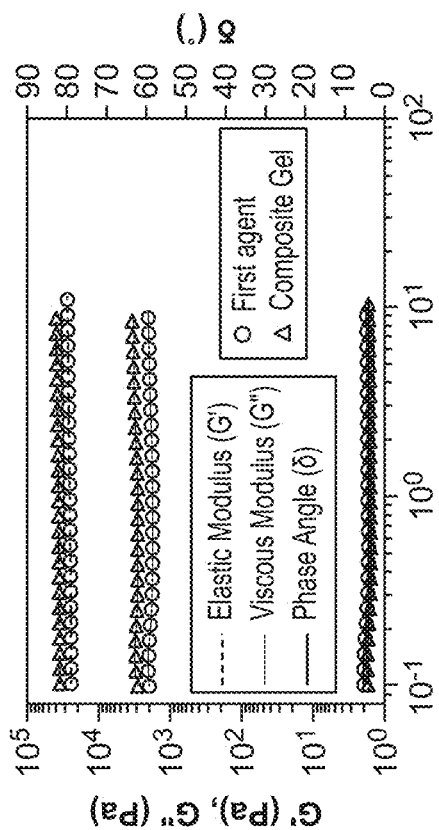
FIG. 5C illustrates graph representing rheological analysis by flow curve analysis of first agent and composite gel.

Further rheological studies like frequency sweep analysis, temperature stability and flow curve analysis were carried out for first agent (110) (Cs gel) and composite (Cs-PA-Ca) gel (100) to show its injectability and shear thinning property. These hydrogels showed G' (elastic modulus) value greater than G" (viscous modulus) and phase angle less than 10° demonstrating its gel like property (FIG. 5A). The hydrogels were also found to be stable over a temperature range of 25 to 50° C. (FIG. 5B). First agent (110) and composite gels (100) showed linear decrease in shear viscosity with increase in shear rate proving its shear thinning property (FIG. 5C).

Figure 5D:
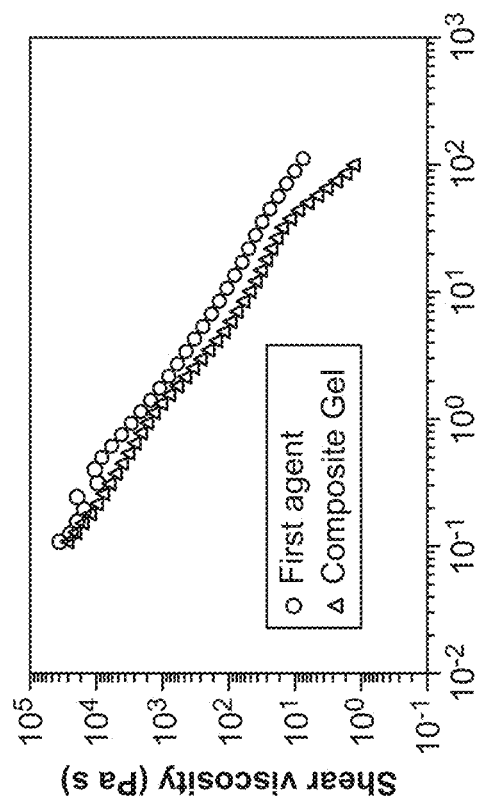
FIG. 5D illustrates bar graph representing rheological analysis by adhesion strength study of first agent and composite gel.

Tissue adhesion strength of first agent (Cs gel) (110) and composite (Cs-PA-Ca) gel (100) was studied by lap shear test according to ASTM Standard F2255-05 Method. Universal tensile machine with load cell of 150 N was used for the study. First agent (110) and composite gel (100) showed adhesion strength of 4-6 kPa and 6-10 kPa respectively (FIG. 5D).

Example 3: Cyto and Hemocompatibility of Developed Hemostatic Agent

Cytocompatibility of different concentrations of first agent (Cs gel) (110), second agent (PA) (110), third agent (Ca) (130) and developed hemostatic composition (Cs-PA-Ca) (100) was studied with HUVEC. The hemostatic composition (100) was incubated with HUVEC for 48 h after which the composition was removed and the percentage cell viability was evaluated by performing alamar blue assay. Hemocompatibility of developed hemostatic composition was also performed. Packed RBCs were diluted in saline to obtain 1% (vol/vol) RBC suspension. RBC suspension was added to the samples and was incubated for 3 h at 37° C., after which the samples were centrifugation, absorbance of the supernatant was read at 540 nm and the percentage hemolysis was calculated.

Figure 6A:
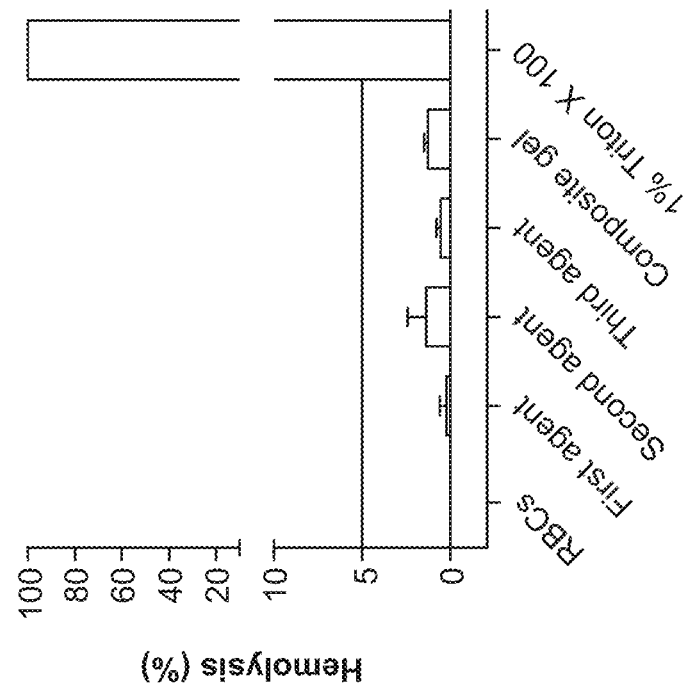
FIG. 6A illustrates bar graph representing the percentage cell viability obtained by the composite gel.
Figure 6B:
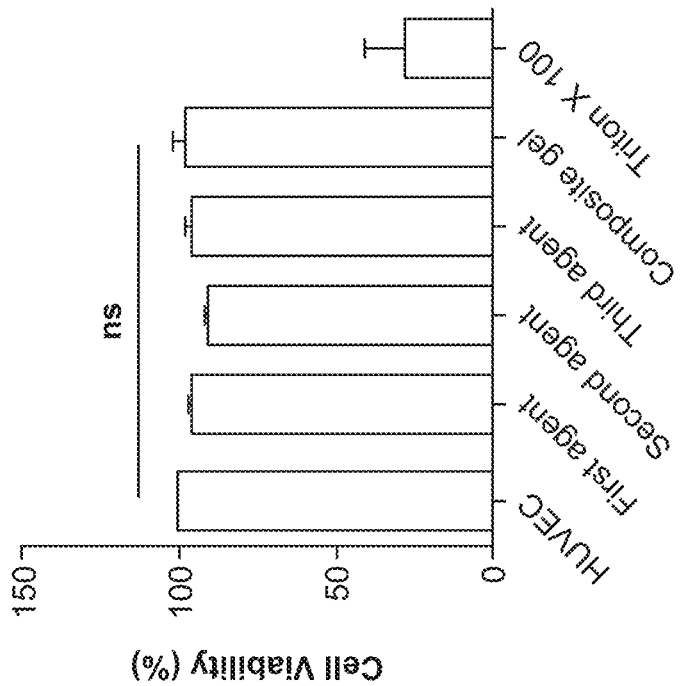
FIG. 6B illustrates bar graph representing the hemolysis obtained by the composite gel.

Results show that the concentration of second agent (PA) (120) and third agent (Ca) (130) up to 0.25% was found to be cytocompatible. Developed hemostatic composition (Cs-PA-Ca) (100) was found to be cytocompatible to HUVEC (FIG. 6A) and was also hemocompatible with less than 5% hemolysis (FIG. 6B)

Example 4: In Vitro Blood Clotting Study

Time taken to clot recalcified whole blood in contact with 1%, 2% and 3% Cs hydrogels; 2% Cs hydrogel with different % PA (0.0625%, 0.125% and 0.25%) and 2% Cs-hydrogel with different % Ca (0.0625%, 0.125%, 0.25% and 0.5%) were evaluated. Anti-coagulated rat whole blood was recalcified by addition of STA®-CaCl2 0.025M solution and this recalcified blood was added to samples taken in plastic micro centrifuge tube. Time taken for stable clot formation was noted by tube inversion method.

Results show that recalcified rat whole blood showed a clotting time of 373±44 s. Of the different concentrations of Cs hydrogel (1% and 2% and 3%) tested, 2% Cs hydrogel exhibited shortest clotting time of 258±34 s (FIG. 7A).

There was no statistical difference in the clotting time of Cs greater than 2%. Therefore, 2% Cs hydrogel was chosen for the study. Different concentration of PA (0.0625%, 0.125%, 0.25% and 0.5%) was added to 2% Cs hydrogel and the clotting time of Cs-PA hydrogel was measured. The 2% Cs-0.25% PA hydrogel showed the least clotting time of 177±9 s (FIG. 7B). Percentage of PA greater than 0.25% did not show statistical difference in its clotting time. Different concentrations of Ca (0.0625%, 0.125%, 0.25% and 0.5%) were then mixed with 2% Cs hydrogel and time of Cs-Ca hydrogel was evaluated. The 2% Cs-0.25% Ca hydrogel showed least clotting time of 157±9 s (FIG. 7C). Percentage of Ca greater than 0.25% did not show statistical difference in blood clotting time. Clotting time of individual components of the prepared composite hydrogel were evaluated in which, 2% Cs-0.25% PA-0.25% Ca hydrogel showed the least clotting time of 112±12 s (FIG. 7D).

Example 5: In Vitro Studies on Mechanism of Action of First, Second and Third Agent in the Developed Hemostatic Composition To confirm the role of first agent (Cs gel) (110) in the hemostatic composition, RBC aggregation study was carried out. RBC was separated from anti-coagulated rat whole blood by centrifugation and was diluted with saline to get 5% (vol/vol) RBC suspension. This RBC suspension was then incubated with the developed hemostatic composition for 5 min at 37° C. After the specific time point samples were washed twice with saline to remove unaggregated RBCs. Aggregated RBCs were then lysed with 1% Triton-X 100 and the absorbance of sample lysate was obtained at 540 nm.

To confirm the role of second agent (PA) (120) in the hemostatic composition, platelet aggregation study was performed by LDH assay. PRP was obtained from anti-coagulated rat whole blood by centrifugation. Developed hemostatic composition was incubated with PRP for 5 min after which the samples were washed to remove unaggregated platelets. Aggregated platelets were then lysed with 1% Triton-X 100 and its absorbance was obtained at 490 nm.

To confirm the role of third agent (Ca) (130) in the hemostatic composition, PT, a PTT and TT studies were performed using ST art 4, Diagnostica Stago, France. PPP was separated from anti-coagulated rat whole blood by centrifugation. PPP was incubated with the developed hemostatic composition for 2 min. For PT study, PPP from incubated sample was added to PT reagent in a cuvette placed in test area of coagulation analyzer and the time taken for PPP to clot was noted as PT. For a PTT study, PPP from incubated sample was further incubated with a PTT reagent after with cuvette was placed in test area and STA®-CaCl2 0.025M solution was added. Time taken for PPP to clot was noted as a PTT. For TT study, PPP from incubated sample was added to TT reagent in a cuvette placed in test area and the time taken for PPP to clot was noted as TT.

Figure 8A:
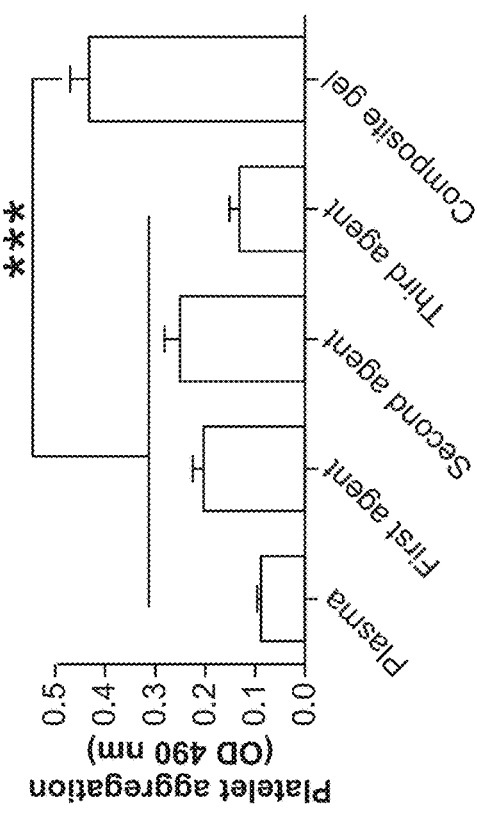
FIG. 8A illustrates bar graph representing the in vitro studies on mechanism of action with RBC aggregation of First agent, Second agent and Third agent in the developed hemostatic composition.
Figure 8B:
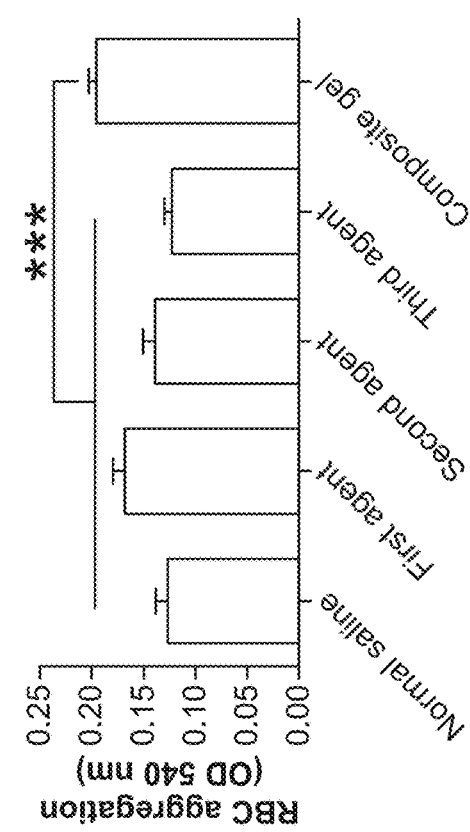
FIG. 8B illustrates bar graph representing the in vitro studies on mechanism of action with Platelet aggregation of First agent, Second agent and Third agent in the developed hemostatic composition.
Figure 8C:
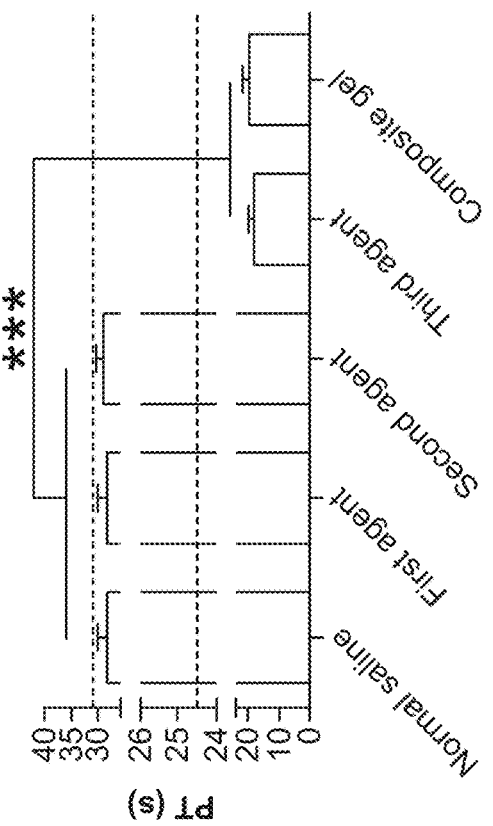
FIG. 8C illustrates bar graph representing the in vitro studies on mechanism of action with PT of First agent, Second agent and Third agent in the developed hemostatic composition.
Figure 8D:
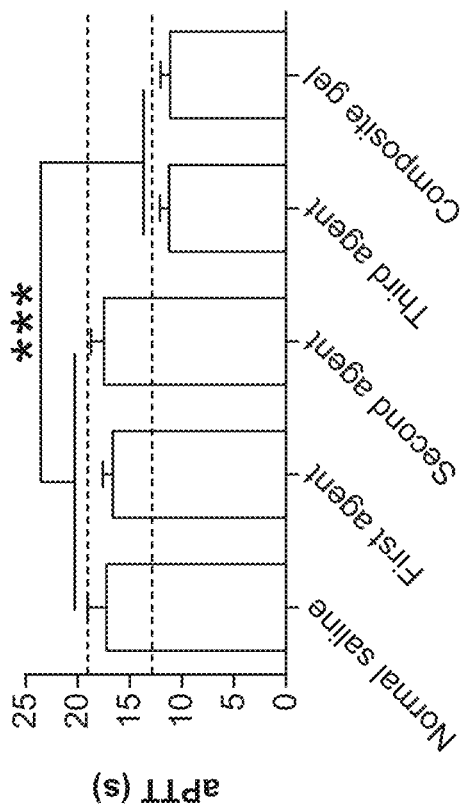
FIG. 8D illustrates bar graph representing the in vitro studies on mechanism of action with aPTT of First agent, Second agent and Third agent in the developed hemostatic composition.
Figure 8E:
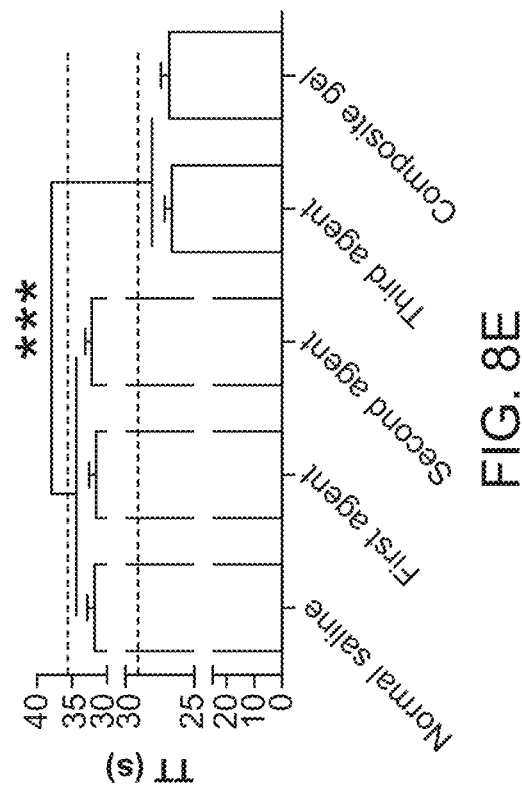
FIG. 8E illustrates bar graph representing the in vitro studies on mechanism of action with TT of First agent, Second agent and Third agent in the developed hemostatic composition.
Figure 9B:
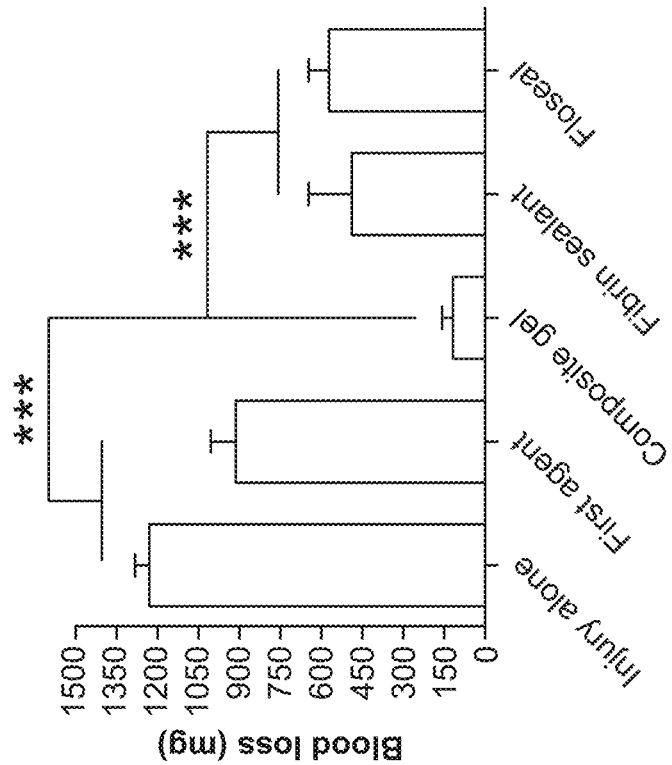
FIG. 9B illustrates bar graph representing mass of blood loss obtained by the developed hemostatic composition in the in vivo evaluation of its hemostatic potential in oozing bleeding condition caused by deep organ injury like liver injury.
Figure 9A:
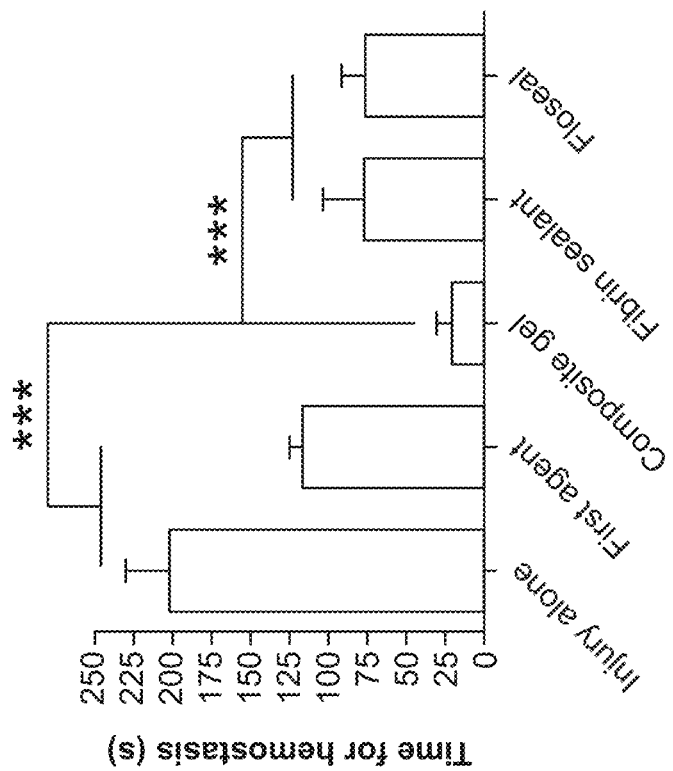
FIG. 9A illustrates bar graph representing time for hemostasis obtained by the developed hemostatic composition in the in vivo evaluation of its hemostatic potential in oozing bleeding condition caused by deep organ injury like liver injury.
Figure 10B:
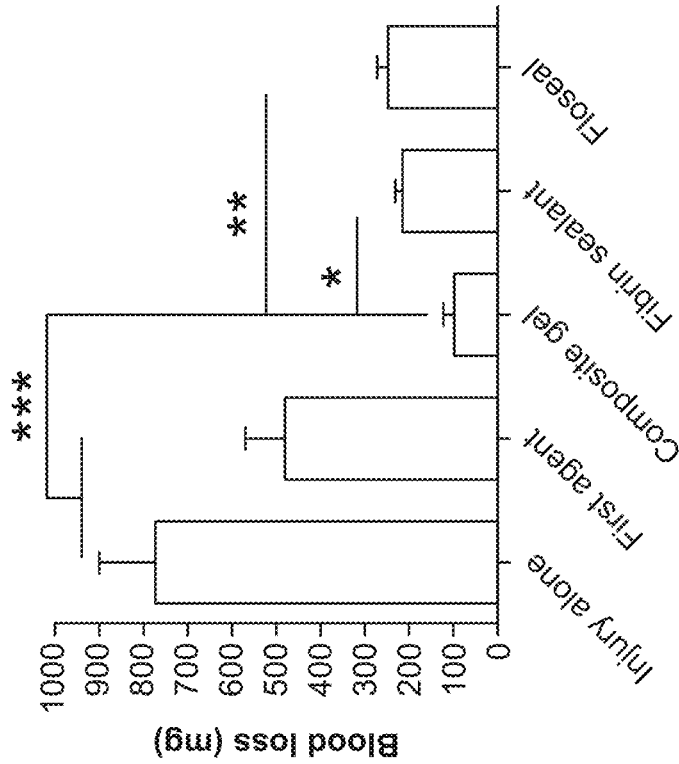
FIG. 10B illustrates bar graph representing the mass of blood loss by the developed hemostatic composition in in vivo evaluation of hemostatic potential in pressured bleeding condition caused by deep organ injury like femoral artery injury.
Figure 10A:
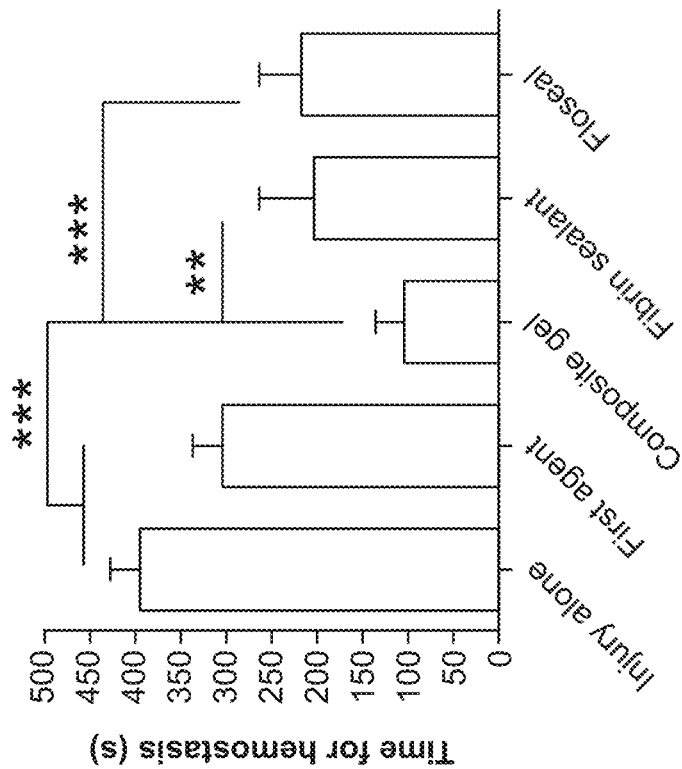
FIG. 10A illustrates bar graph representing the time for hemostasis by the developed hemostatic composition in in vivo evaluation of hemostatic potential in pressured bleeding condition caused by deep organ injury like femoral artery injury.

Result clearly show the mechanistic role of first agent (110) in RBC aggregation study in which the first agent (110) showed higher RBC aggregation compared to second (120) and third agents (130). The developed hemostatic composition (100) showed significantly higher RBC aggregation because of the presence of first (110) and second agents (120) (FIG. 8A). Similarly in platelet aggregation study, the second agent (120) showed higher platelet aggregation compared to first (120) and third agents (130). The developed hemostatic composition (100) showed significantly higher platelet aggregation because of the presence of all the three agents (FIG. 8B). Developed hemostatic composition (100) and third agent (130) showed shorter PT, a PTT and TT values mainly because of the role of third agent of the hemostatic composition (100) (FIG. 8C-E).

Example 6: In Vivo Evaluation of the Hemostatic Potential of the Developed Hemostatic Agent in Liver Injury (Oozing Bleeding) Created in Rat Model Procedure:-Male Sprague-Dawley rats were selected for the study. Liver injury was created by puncturing liver using a 5 mm biopsy punch. Upon initiation of bleeding, the developed hemostatic agent or commercial agent (fibrin glue or floseal) were applied to the injured site and time to achieve hemostasis was evaluated. No compression was applied at the bleeding site to control blood loss. All animals after study were euthanized. Pre-weighed gauze pieces were used to collect the blood lost due to the injury. Amount of blood loss and time to achieve hemostasis were evaluated from the study.

Results clearly show that the developed hemostatic composition (2% Cs-0.25% PA-0.25% Ca hydrogel) (100) brings about rapid bleeding control with shortest time to achieve effective hemostasis (10-30 s) and mass of blood loss (70-155 mg) compared to sham control, chitosan gel (2% Cs hydrogel) and also commercial hemostatic composition fibrin glue and floseal when treated on oozing bleeding condition in rat model. Interaction of PA and Ca with Cs hydrogel has shown significance of $P<0.05$% ($P=0.0403$) which implies that addition of 0.25% PA and 0.25% Ca in 2% Cs hydrogel has shown synergistic effect in reducing the time taken to achieve hemostasis and amount of blood loss in liver injury model.

Example 7: In Vivo Evaluation of the Hemostatic Potential of the Developed Hemostatic Agent in Femoral Artery Injury (Pressured Bleeding) Created in Rat Model Procedure: Male Sprague-Dawley rats were selected for the creation of femoral artery injury. The injury was created by puncturing femoral artery using a 24G needle. Upon initiation of bleeding, the developed hemostatic agent (100) and commercial agent (fibrin glue or floseal) were applied to the injured site and time to achieve hemostasis was evaluated. No compression was applied at the bleeding site to control blood loss. All animals after study were euthanized. Pre-weighed gauze pieces were used to collect the blood lost due to the injury. Amount of blood loss and time to achieve hemostasis were evaluated from the study.

Results clearly show that the developed hemostatic agent (2% Cs-0.25% PA-0.25% Ca hydrogel) (100) brings about rapid bleeding control with least time taken for hemostasis (70-140 s) and mass of blood loss (70-130 mg) compared to sham control, chitosan gel (2% Cs gel) and also commercial hemostatic composition fibrin glue and floseal, when treated on pressured bleeding condition in rat model. Interaction of PA and Ca with Cs hydrogel has shown significance of $P<0.05$% ($P=0.0318$) which implies that addition of 0.25% PA and 0.25% Ca in 2% Cs hydrogel has shown synergistic effect in reducing the time taken to achieve hemostasis and amount of blood loss in femoral artery injury model. The developed hemostatic agent could adhere at the site of application in-spite of pressured bleeding from the injured site.

Figures 11A, 11B, 11C:
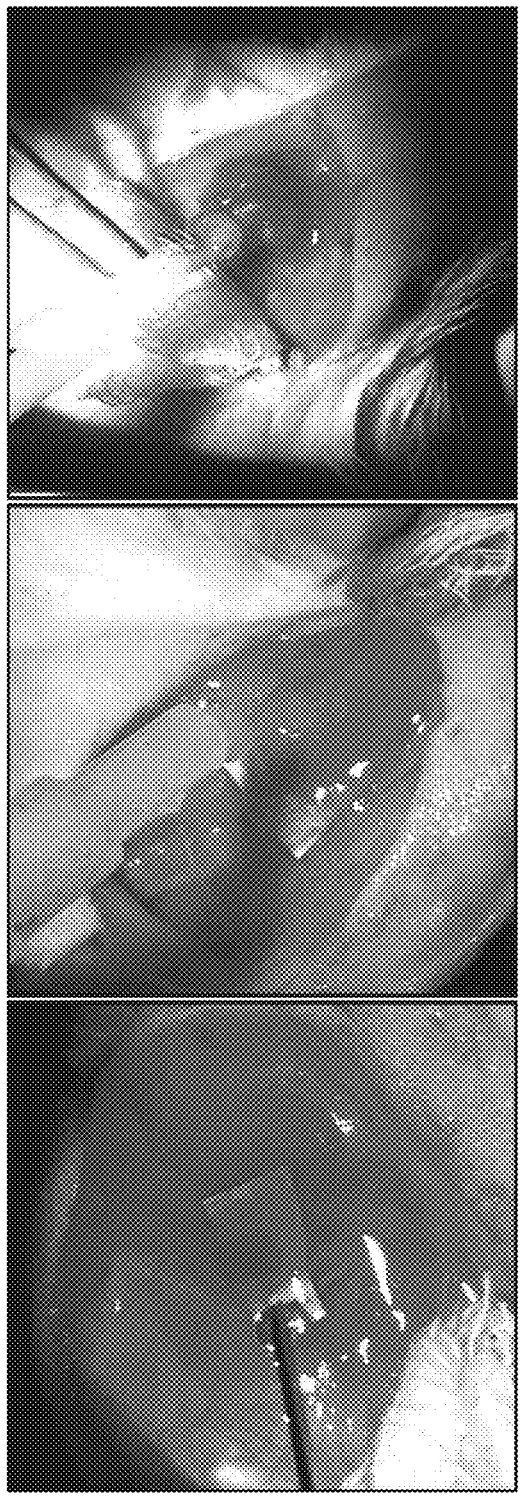
FIG. 11A illustrates comparison of the efficiency of Fibrin sealant applied on femoral artery hemorrhage model.
FIG. 11B illustrates comparison of the efficiency of Floseal applied on femoral artery hemorrhage model.
FIG. 11C illustrates comparison of the efficiency of Cs-PA-Ca hydrogel applied on femoral artery hemorrhage model.

Example 8: Comparison of Developed Hemostatic Composition (Cs-PA-Ca Hydrogel) with Commercial Hemostatic Agents in in Vivo Femoral Artery Injury Model Observations during surgical procedure is that when Fibrin sealant was used to control bleeding in pressured bleeding condition, the fibrinogen and thrombin solutions flowed along with blood and couldn't stay firmly, due to which there was a delay in stable fibrin formation at the site of application (FIG. 11A). Floseal as it's in a granular form when applied at the injury site also was washed away by blood and couldn't stay firmly in pressured bleeding condition (FIG. 11B). The developed Cs-PA-Ca composite hydrogel (100) due to its muco adhesive and shear thinning property retained at the site of application and helped in achieving bleeding control in a shorter time and with least amount of blood loss compared to its individual components and commercial products even without compression (FIG. 11C).

Example 9: In Vivo Toxicological Evaluation of Developed Hemostatic Agent in Liver Injury Created in Rat Model Procedure: Male Sprague-Dawley rats were selected for the creation of liver injury. The injury was created using a 5 mm biopsy punch. Upon initiation of bleeding, hydrogel was applied on the bleeding site. Once the bleeding stops, abdomen was sutured. Animals were allowed to recover. After 1 and 8 weeks post-surgery animals were euthanized and liver was collected in 10% formalin solution. It was then processed for H&E analysis. Hydrogel systems tested are floseal, first agent (Cs) and composite (Cs-PA-Ca) hydrogel.

Results show that even after 8 weeks, material retention was seen due to slow degradation property of first agent (110) and developed hemostatic composition (100) when left at the site of application, inflammatory response like fibrosis, micro abscess formation and granulation tissue was observed (FIG. 12).

In conclusion, the developed hemostatic composition (100) was prepared and characterized using FESEM, EDAX and FTIR analysis. Developed hemostatic composition (100) showed injectability and shear thinning property. Adhesion strength of the composite hydrogel was also evaluated. The in vitro results show the cyto and hemocompatible nature of developed hemostatic composition. Concentration of first (110), second (120) and third agent (130) was optimized by performing in vitro blood clotting study. In vitro mechanistic studies confirm the role of each of the agent (Cs, PA and Ca) that constitute the hemostatic composition (100). Further in vivo results demonstrate that the developed hemostatic agent (2% Cs-0.25% PA-0.25% Ca) (100) is able to bring about effective bleeding control in shorter duration with least amount of blood loss in both oozing and pressured bleeding conditions in deep organ injuries in rat model. Compared to commercial hemostatic agents like Fibrin sealant and Floseal the developed hemostatic agent due to its shear thinning and adhesion property, could stay firmly at site of application and achieve rapid hemostasis. In vivo toxicological evaluation reveals the retention of the applied hemostatic composition at the site of application even after 8 weeks of surgery. Therefore, the developed hemostatic composition (100) when used as hemostatic agent should always be removed completely by gentle irrigation from the site of application once hemostasis is achieved.

We claim:

1. A hemostatic hydrogel composition for rapid and synergistic bleeding control consisting essentially of: 0.01% to 2% of chitosan; 0.01% to 0.25% of potassium aluminum sulphate; and 0.01% to 0.25% of a calcium salt; wherein the clotting time of the composition is in the range of 10s to 140s.

2. The composition as claimed in claim 1, wherein said hydrogel is formed into a shape selected from sponge, flexible bandage, scaffold, injectable gel, foam, and cream.

3. The composition as claimed in claim 1, wherein said composition is stable in the temperature range 25 to 50° C.

4. The composition as claimed in claim 1, wherein said composition exhibits a hemolytic potential of less than 5 percent, wherein the hemolytic potential is measured by a method comprising i) centrifuging a red blood cell suspension incubated with the composition, positive control or negative control for 3 hours at 37° C. to obtain respective supernatants; measuring the absorbance of the respective supernatants at 540 nm; computing the hemolytic potential by comparing the absorbances of the composition with that of the positive and negative control.

5. The composition as claimed in claim 1, wherein said composition exhibits an RBC aggregation, wherein the RBC aggregation is at least 0.2 as expressed in terms of optical density at 540 nm.

6. The composition as claimed in claim 1, wherein said composition exhibits a platelet aggregation, wherein the platelet aggregation is at least 0.4 as expressed in terms of optical density at 490 nm.

7. The composition as claimed in claim 1, wherein said composition exhibits an adhesion strength of 6-10 kPa, as measured by lap shear test according to ASTM Standard F2255-05 method.

8. The composition as claimed in claim 1, wherein the chitosan has molecular weight in the range of 25 kDa to 1000 kDa, an average degree of deacetylation between 40% to about 99%.

9. The composition as claimed in claim 1, comprising: 2% chitosan; 0.25% potassium aluminum sulphate; and 0.25% calcium salt.

10. The composition as claimed in claim 9, wherein the clotting time of the composition is in the range of 10s to 30s in case of oozing bleeding, wherein the clotting time of the composition is in the range of 70-140s in case of pressured bleeding.

11. The composition as claimed in claim 1, wherein the clotting time of the composition is in the range of 10s to 30s in case of oozing bleeding, wherein the clotting time of the composition is in the range of 70-140s in case of pressured bleeding.

12. A method of preparing the composition as claimed in claim 1, comprising the steps of:
adding 0.01% to 2% of chitosan powder in acetic acid under continuous stirring to form a chitosan solution;
adding sodium hydroxide to the chitosan solution under continuous stirring to adjust the pH to be in the range of 6 to 7;
centrifuging the solution to form a chitosan hydrogel;
mixing 0.01% to 0.25% of potassium aluminum sulphate to chitosan hydrogel under vigorous stirring to form a homogeneous mixture;
adding 0.01% to 0.25% calcium chloride to the homogeneous mixture under vigorous stirring to obtain the homogenous mixture of composite hydrogel.

\* \* \* \* \*